United States Patent [19]

Henning et al.

[11] Patent Number: 4,778,793
[45] Date of Patent: Oct. 18, 1988

[54] DIHYDROQUINOLINONE DERIVATIVES, PROCESSES FOR THEIR PREPARATION, MEDICAMENTS CONTAINING THEM AND THEIR USE, AND INTERMEDIATE PRODUCTS FOR THEIR PREPARATION

[75] Inventors: Rainer Henning, Hattersheim am Main; Ulrich Lerch, Hofheim am Taunus; Joachim Kaiser, Frankfurt am Main, all of Fed. Rep. of Germany

[73] Assignee: Hoechst Aktiengesellschaft, Frankfurt, Fed. Rep. of Germany

[21] Appl. No.: 886,740

[22] Filed: Jul. 18, 1986

[30] Foreign Application Priority Data

Jul. 20, 1985 [DE] Fed. Rep. of Germany ....... 3526044

[51] Int. Cl.[4] .................. A61K 31/495; C07D 401/12
[52] U.S. Cl. .................... 514/253; 514/312; 514/235.2; 544/128; 544/295; 544/363; 546/128
[58] Field of Search ........ 544/295, 363, 128; 546/90, 158; 514/258, 234, 312

[56] References Cited

U.S. PATENT DOCUMENTS

3,551,413 12/1970 Krapcho .............. 546/158
4,071,520 1/1978 Wehrmeister ........ 546/158

FOREIGN PATENT DOCUMENTS

2007468 9/1970 Fed. Rep. of Germany.
6516320 6/1966 Netherlands.
1042638 9/1966 United Kingdom.
1305278 1/1973 United Kingdom.

*Primary Examiner*—Glennon H. Hollrah
*Assistant Examiner*—James H. Turnipseed
*Attorney, Agent, or Firm*—Finnegan, Henderson, Farabow, Garrett and Dunner

[57] ABSTRACT

Compounds of the formula I

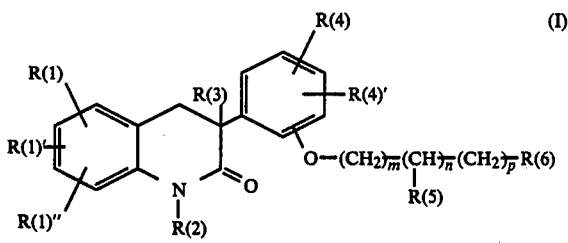

where $R(1)$, $R(2)$, $R(3)$, $R(4)$ and $R(5)$ are, inter alia, hydrogen and alkyl, m is 1–4, n is 0 or 1, p is 0–4 and $R(6)$ is identical or different dialkylamine derivatives, and salts thereof, have a calcium-antagonistic action. They are obtained by reacting corresponding amines with a compound II which carries, on the side chain, a leaving group which can be displaced nucleophilically, or from a hydroxyphenyl-dihydroquinolin-2-one compound by reaction with a corresponding side chain compound which has a leaving group which can be displaced nucleophilically.

6 Claims, No Drawings

DIHYDROQUINOLINONE DERIVATIVES, PROCESSES FOR THEIR PREPARATION, MEDICAMENTS CONTAINING THEM AND THEIR USE, AND INTERMEDIATE PRODUCTS FOR THEIR PREPARATION

It is known that compounds which prevent the flow of calcium ions into cells can be used as therapeutics for the treatment of various diseases, in particular of the cardiovascular system, in humans and other warm-blooded animals.

British patent No. 1,305,278 and German Offenlegungsschrift No. 2,007,468 describe 3,4-dihydro-3-phenyl-1-methyl-quinolin-2-ones as stimulants of the central nervous system.

1-(2-Dimethylaminoethyl)-3-phenyl-tetrahydroquinolin-2-one is mentioned as having an antihypertensive action in Dutch patent application No. 6,516,320.

However, no quinolin-2-ones with a calcium-antagonistic action and likewise none of the compounds according to the invention have yet been described.

The invention relates to dihydroquinolinone derivatives of the formula I, which have a calcium-antagonistic action,

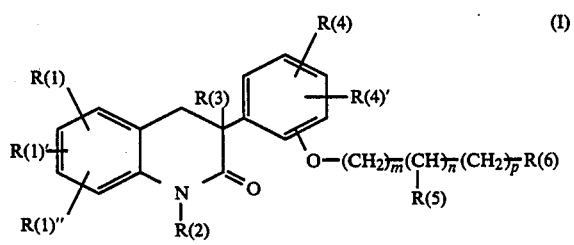

and in which
R(1), R(1)' and R(1)" are identical or different and independent of one another and denote hydrogen, $(C_1-C_4)$-alkyl, $(C_1-C_3)$-alkoxy, F, Cl, $CF_3$, nitro, hydroxyl, acetamido or amino, or R(1) and R(1)' together denote $(C_1-C_2)$-alkylenedioxy,
R(2) denotes hydrogen, straight-chain or branched $(C_1-C_{10})$-alkyl or straight-chain or branched $(C_3-C_{10})$-alkenyl,
R(3) denotes hydrogen, straight-chain or branched $(C_1-C_{10})$-alkyl, straight-chain or branched $(C_3-C_{10})$-alkenyl, $(C_4-C_8)$-cycloalkyl, $(C_4-C_8)$-cycloalkyl-$(C_1-C_4)$-alkyl or phenyl-$(C_1-C_4)$-alkyl, the phenyl radical being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy and nitro,
R(4) and R(4)' are identical or different and independently of one another denote hydrogen, $(C_1-C_4)$-alkyl, $(C_1-C_3)$-alkoxy, F, Cl, $CF_3$, nitro, hydroxyl, acetamido or amino,
R(5) denotes hydrogen, hydroxyl or $(C_1-C_3)$-alkyl,
m denotes 1, 2, 3 or 4,
n denotes 0 or 1,
p denotes 0, 1, 2, 3 or 4 and
R(6) denotes one of the following groups

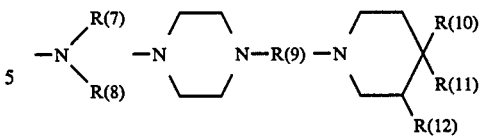

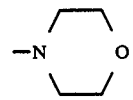

in which
R(7) and R(8) are identical or different and independently of one another denote hydrogen, $(C_1-C_{10})$-alkyl, $(C_4-C_8)$-cycloalkyl, $(C_4-C_8)$-cycloalkyl-$(C_1-C_4)$-alkyl, phenyl-$(C_1-C_6)$-alkyl, the phenyl radical being unsubstituted or substituted by one, two or three radicals from the group comprising $(C_1-C_4)$-alkylenedioxy, F, Cl, $CF_3$ and hydroxyl, or pyridyl-$(C_1-C_4)$-alkyl,
R(9) denotes hydrogen, straight-chain or branched $(C_1-C_{10})$-alkyl, phenyl, phenyl-$(C_1-C_4)$-alkyl or diphenyl-$(C_1-C_5)$-alkyl, phenyl-$(C_1-C_4)$-alkanoyl, benzoyl, the phenyl radical in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, $CF_3$ and hydroxyl, or pyridyl, pyrimidinyl or $(C_1-C_5)$-alkanoyl,
R(10) denotes hydrogen, $(C_1-C_{10})$-alkyl, phenyl, phenyl-$(C_1-C_4)$-alkyl, the phenyl radical in each case being unsubstituted or substituted by one, two or three radicals from the group comprising $(C_1-C_4)$-alkyl, $(C_1-C_4)$-alkoxy, $(C_1-C_2)$-alkylenedioxy, F, Cl, $CF_3$ and hydroxyl,
R(11) denotes hydrogen, hydroxyl or $(C_1-C_4)$-alkoxy, or together with R(12) denotes a bond, and
R(12) denotes hydrogen, or together with R(11) denotes a bond;
and the salts of the compounds of the formula I with pharmaceutically acceptable acids.

Preferred compounds of the formula I are those in which
R(1) and R(1)' are identical or different and independently of one another denote hydrogen, methyl, ethyl, methoxy, ethoxy, fluorine, chlorine, $CF_3$, nitro or acetamido; or together denote $(C_1-C_2)$alkylenedioxy,
R(1)" denotes hydrogen,
R(2) denotes hydrogen or straight-chain or branched $(C_1-C_6)$-alkyl,
R(3) denotes hydrogen, straight-chain or branched $(C_1-C_6)$-alkyl, allyl, cyclopentyl, cyclohexyl, benzyl or phenethyl, in each case unsubstituted or substituted by $(C_1-C_3)$-alkyl, $(C_1-C_3)$-alkoxy, F, Cl, $CF_3$, $(C_1-C_2)$-alkylenedioxy or nitro,
R(4) denotes hydrogen, methyl, methoxy, ethoxy, chlorine, nitro, hydroxyl, acetamido or amino,
R(4)' denotes hydrogen,
R(5) denotes hydrogen or hydroxyl,
m denotes 1, 2 or 3,
n denotes 0 or 1,
p denotes 1, 2, 3 or 4 and
R(6) denotes one of the following groups

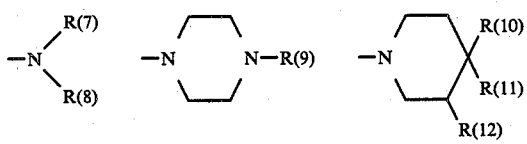

in which
R(7) denotes hydrogen, methyl, ethyl, propyl or isopropyl,
R(8) denotes hydrogen, methyl, ethyl, propyl, isopropyl, cyclopentylethyl, cyclohexylethyl, phenyl-($C_1$-$C_4$)-alkyl, the phenyl radical being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, $CF_3$ and hydroxyl, or pyridyl-($C_1$-$C_4$)-alkyl,
R(9) is as defined above,
R(10) denotes phenyl or phenyl-($C_1$-$C_4$)-alkyl, the phenyl radical in each case being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, $CF_3$ and hydroxyl,
R(11) denotes hydrogen, hydroxyl or methoxy, or together with R(12) denotes a bond, and
R(12) denotes hydrogen, or together with R(11) denotes a bond;
and the salts of these compounds of the formula I with pharmaceutically acceptable acids.

Particularly preferred compounds of the formula I are those in which
R(1) denotes hydrogen, methyl, methoxy, fluorine or chlorine,
R(1)' and R(1)" denote hydrogen,
R(2) denotes hydrogen, methyl or ethyl,
R(3) denotes hydrogen, methyl, ethyl, propyl, isopropyl, butyl, sec.-butyl, isobutyl, allyl, cyclopentyl, cyclohexyl, benzyl or phenethyl, the phenyl ring in each case being unsubstituted or substituted by methyl, methoxy, chlorine, fluorine, methylenedioxy or nitro,
R(4) denotes hydrogen, methyl, methoxy, chlorine, nitro or hydroxyl,
R(4)' denotes hydrogen,
R(5) is as defined above,
m denotes 0 or 1,
n denotes 0 or 1,
p denotes 1, 2, 3 or 4 and
R(6) denotes one of the following groups

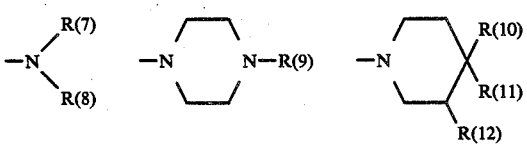

in which
R(7) denotes hydrogen or methyl,
R(8) denotes phenyl-($C_1$-$C_4$)-alkyl, the phenyl radical being unsubstituted or substituted by one, two or three radicals from the group comprising methyl, methoxy, chlorine, methylenedioxy and hydroxyl,
R(9) is as defined above,
R(10) denotes phenyl or phenyl-($C_1$-$C_2$)-alkyl, the phenyl radical in each case being unsubstituted or substituted by one, two or three radicals from the group comprising methyl, methoxy, chlorine, methylenedioxy and hydroxyl,
R(11) denotes hydrogen, hydroxyl or methoxy, or together with R(12) denotes a bond, and
R(12) denotes hydrogen, or together with R(11) denotes a bond;
and the salts of these compounds of the formula I with pharmaceutically acceptable acids.

Possible such pharmaceutically acceptable acids are inorganic acids, such as hydrochloric acid, hydrobromic acid, hydriodic acid, sulfuric acid, phosphoric acid or nitric acid, or organic acids, such as tartaric acid, malic acid, lactic acid, maleic acid, fumaric acid, malonic acid, oxalic acid, gluconic acid, camphorsulfonic acid, benzenesulfonic acid, acetic acid, propionic acid or p-toluenesulfonic acid.

Especially preferred compounds of the formula I are those as defined above in which
R(1) denotes hydrogen, methyl, methoxy, fluorine or chlorine,
R(1)' and R(1)" denote hydrogen,
R(2) denotes hydrogen or methyl,
R(3) denotes methyl, ethyl, propyl, isopropyl, butyl, sec.-butyl, isobutyl, cyclopentyl, cyclohexyl or benzyl, unsubstituted or substituted by methoxy, methyl, fluorine, chlorine or nitro,
R(4) denotes hydrogen, methoxy, methyl or chlorine,
R(5) denotes hydrogen or hydroxyl,
m denotes 0 or 1,
n denotes 0 or 1,
p denotes 1, 2, 3 or 4,
R(6) denotes one of the following groups

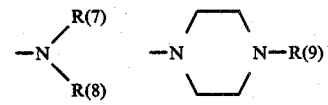

R(7) denotes methyl,
R(8) denotes phenyl-($C_1$-$C_4$)-alkyl, the phenyl radical being unsubstituted or substituted by one, two or three radicals from the group comprising methyl, methoxy, chlorine, methylenedioxy and hydroxyl,
R(9) denotes phenyl-($C_1$-$C_4$)-alkyl, the phenyl radical being unsubstituted or substituted by one, two or three radicals from the group comprising ($C_1$-$C_2$)-alkoxy, ($C_1$-$C_2$)-alkylenedioxy and hydroxyl, or diphenyl-($C_1$-$C_4$)-alkyl, the phenyl radicals being unsubstituted or substituted by chlorine, fluorine or methoxy,
and physiologically acceptable salts thereof.

Unless indicated otherwise, halogen denotes fluorine or chlorine.

The compounds of the formula I have asymmetric C atoms and can therefore occur as enantiomers or diastereomers. The invention relates both to the pure isomers and to mixtures thereof. Mixtures of diastereomers can be resolved into the components by customary methods, for example by selective crystallization from suitable solvents or chromatography on silica gel or aluminum oxide. Racemates can be resolved into the individual enantiomers by customary methods, thus, for example, by salt formation with optically active acids, such as camphorsulfonic acid or dibenzoyltartaric acid, and selective crystallization, or by derivatization with suitable optically active reagents, separation of the diastereomeric derivatives and cleavage to give the underivatized compound again.

The invention furthermore relates to a process for the preparation of compounds of the formula I, which comprises (a) reacting a compound of the formula II

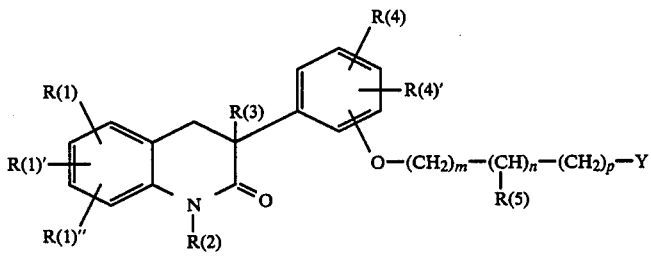

in which R(1), R(1)', R(1)", R(2), R(3), R(4), R(4)', R(5), m, n and p have the same meaning as in formula I, and in which Y denotes a leaving group which can be displaced nucleophilically, in particular a Cl, Br or I atom, or a sulfonic acid radical, preferably a methanesulfonyl radical, a benzenesulfonyl radical, a toluenesulfonyl radical or a trifluoromethanesulfonyl radical, with one of the compounds of the formulae IIIa, IIIb, IIIc or IIId,

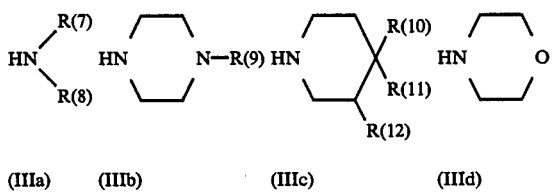

(IIIa)   (IIIb)   (IIIc)   (IIId)

in which R(7), R(8), R(9), R(10), R(11) and R(12) have the same meaning as in formula I, under nucleophilic substitution conditions, preferably in a polar organic solvent, such as an alcohol, preferably methanol, ethanol, propanol or isopropanol, or a lower ketone, preferably acetone or methyl ethyl ketone, or dimethylformamide, dimethylsulfoxide or sulfolane or a hydrocarbon, preferably toluene, in the presence or absence of an auxiliary base for trapping the acid formed, preferably in the presence of potassium carbonate, sodium carbonate, triethylamine, N-ethylmorpholine or pyridine, at a temperature between 0° and 160° C., preferably between 20° and 120° C., or which comprises (b) reacting a compound of the formula IV

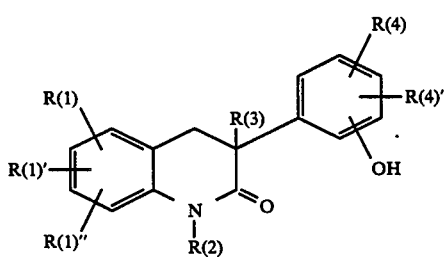

in which R(i), R(i)', R(1)", R(2), R(3), R(4) and R(4)' have the same meaning as in formula I, with a compound of the formula V

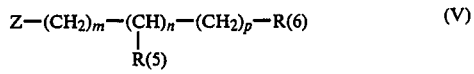

in which Z is defined in the same way as Y in formula (II)

II, and in which R(5), R(6), m, n and p have the same meaning as in formula I, either in a polar aprotic solvent, such as dimethylformamide, dimethylsulfoxide, tetrahydrofuran, sulfolane or N-methylpyrrolidone, in the presence of a strong base, such as sodium hydride, potassium hydride, sodium amide, lithium diisopropylamide, butyl-lithium or lithium hexamethyldisilazide, at a temperature between −40° and +60° C., preferably between −10° and +30° C., or in a protic or aprotic polar organic solvent, such as a lower alcohol, for example methanol, ethanol or isopropanol, or a lower ketone, preferably acetone or methyl ethyl ketone, or in dimethylformamide, in the presence of a weak to medium-strength base, such as an alkali metal hydroxide or carbonate or alkaline earth metal hydroxide or carbonate or an amine, such as, for example, triethylamine, N-ethylmorpholine, N-methyldiisopropylamine or pyridine, at a temperature between 0° and 160° C., preferably between 20° and 120° C.

Compounds of the formula II are obtained by reacting 2-nitrobenzaldehydes of the formula VI, in which R(1), R(1)' and R(1)" have the same meaning as in formula I

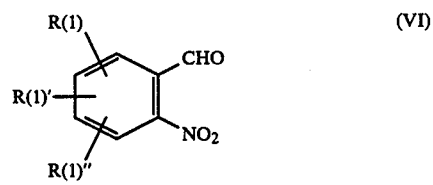

with phenylacetic acids of the formula VII

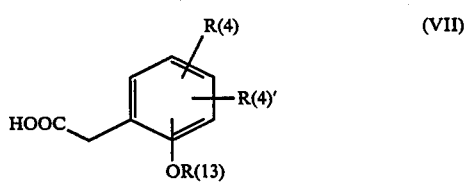

in which R(4) and R(4)' have the same meaning as in formula I and R(13) represents a radical which can be split off under mild conditions, such as, for example, a methyl, benzyl or acetyl radical, in acetic anhydride at 60° to 130° C. with or without the addition of a tertiary amine, such as, for example, tripropylamine, diisopropylethylamine or N-methylmorpholine, compounds of the formula VIII being obtained

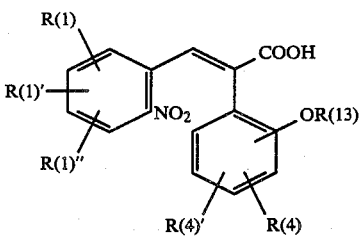

(VIII)

Hydrogenation with a noble metal catalyst, such as, for example, palladium-on-animal charcoal, or with Raney nickel in an alcoholic solvent or an ester, such as, for example, ethanol or ethyl acetate, under an $H_2$ pressure of 1 to 30 bar at 0° to 60° C. gives compounds of the formula IX

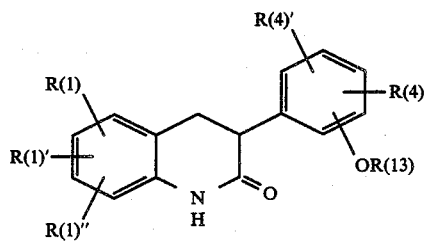

(IX)

Alkylation on the nitrogen is carried out by reaction with a base, such as potassium carbonate or an alkali metal hydride, and an alkyl halide of the formula R(2)-Hal, in which R(2) is as defined for formula I and Hal denotes Cl, Br or iodine, to give compounds of the formula X

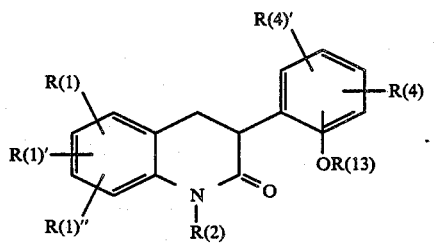

(X)

Radicals R(3) can be introduced into compounds of the formula X by alkylation with an alkyl halide of the formula R(3)-Hal, in which R(3) is as defined for formula I and Hal denotes Cl, Br or iodine, in the presence of a strong base, such as sodium hydride, potassium hydride or an alkali metal amide, compounds of the formula XI being obtained:

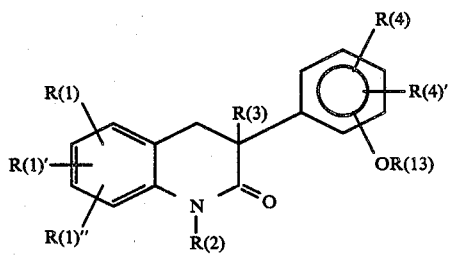

(XI)

The protective group R(13) is then split off under suitable conditions, thus, for example, by catalytic hydrogenation for the benzyl group or reaction with boron tribromide, trimethyliodosilane or pyridine hydrochloride for the methyl group or potassium carbonate in alcoholic solution for the acetyl group. Compounds of the formula IV are formed.

The compounds of the formula IV can then be reacted with a compound of the formula XII

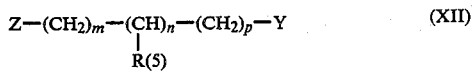

in which R(5), m, n and p have the same meaning as in formula I, Y has the same meaning as in formula II and Z has the same meaning as Y, Z and Y being identical or different, under the conditions described for process variant (b) to give the compounds of the formula II.

Compounds of the formula V are obtained in a manner which is known per se from compounds of the formulae IIIa, IIIb, IIIc or IIId by reaction with compounds of the formula XII under the conditions described for process variant (a).

The compounds of the formula I according to the invention have pharmacological and biochemical actions, in particular calcium-antagonistic actions, and can therefore be used for the treatment of all disease conditions based on a disturbance of the calcium balance in a warm-blooded animal.

Their calcium-antagonistic activity can be demonstrated on the biochemical test model of displacement of tritium-labeled nitrendipine.

In this, membrane preparations containing isolated calcium channels are charged with the labeled substance. After incubation with the test substance, the radioactivity released in the supernatant solution is determined. In this model, the compounds of the formula I according to the invention have $IC_{50}$ values from $10^{-6}$ molar to $10^{-10}$ molar.

In other test models with which a calcium-antagonistic action can be demonstrated, for example by the coronary flow in the isolated guinea-pig heart or by the action potential of the isolated guinea-pig papillary muscle, the compounds of the formula I likewise have a potent action.

The compounds of the formula I according to the invention and their pharmacologically acceptable salts reduce the flow of calcium ions into cells and are therefore suitable for the treatment of the cardiovascular system in the event of appropriate complaints, such as, for example, for various forms of angina pectoris, tachycardia, disorders in cardiac rhythm and hypertension. They are active within a wide dose range. The level of the dose administered depends on the nature of the treatment desired, on the mode of administration and on the condition, type and size of the mammal treated. With oral dosage, satisfactory results are achieved with doses from 0.01, preferably from 0.1 and in particular from 0.5 mg up to 100 mg, preferably up to 20 mg and in particular up to 15 mg, of a compound of the formula I per kg of body weight. The daily dose for humans varies from at least 10 and in particular 20 mg up to not more than 800 mg, preferably 500 mg, it being possible for individual doses of 5 to 200 mg, in particular 5–100 mg, to be administered, preferably one to three times daily.

The dose for intravenous and intramuscular administration is at least 1 mg, preferably 5 and not more than 300 mg, preferably 150 mg, daily.

The pharmacologically usable compounds of the present invention and their salts can be used for the preparation of pharmaceutical products which contain an effective amount of the active substance together with excipients and which are suitable for enteral and parenteral administration. Tablets or gelatin capsules which contain the active compound together with diluents, for example lactose, dextrose, sucrose, mannitol, sorbitol, cellulose and/or glycine, and lubricants, such as silica, talc, stearic acid or salts thereof, such as magnesium stearate or calcium stearate, and/or polyethylene glycol, are preferably used. Tablets also contain binders, such as magnesium aluminum silicate, starch, gelatin, tragacanth, methylcellulose, sodium carboxymethylcellulose and/or polyvinylpyrrolidone, and, if required, a colorant, flavor substances and sweeteners. Injectable solutions are preferably isotonic aqueous solutions or suspensions which can be sterilized and can contain auxiliaries, such as preservatives, stabilizers, wetting agents, emulsifying agents, solubilizing agents, salts for regulating the osmotic pressure and/or buffer substances. The pharmaceutical products according to the invention, which, if desired, can contain further pharmacologically useful substances, are prepared, for example, by means of conventional mixing, granulating and coating processes and contain 0.1% to about 75%, preferably about 1% to about 50%, of the active compound.

The examples which follow are intended to illustrate the invention without limiting it to these examples.

EXAMPLE 1

1H-3,4-Dihydro-3-(2-methoxyphenyl)-quinolin-2-one (a) 2-(2-Methoxyphenyl)-3-(2-nitrophenyl)-2-propenoic acid 25 g of 2-nitrobenzaldehyde, 28 g of 2-methoxyphenylacetic acid and 0.16 mol of diisopropylethylamine are boiled under reflux in 90 ml of acetic anhydride under nitrogen for 8 hours. After cooling to 60° C., the mixture is poured onto 200 ml of hot water. The mixture is stirred for a further 2 hours, while cooling, and the product is filtered off with suction and washed with a little cold ethanol. Recrystallization from ethanol gives 38.7 g of the title compound of melting point 217°–219° C.

(b) 1H-3,4-Dihydro-3-(2-methoxyphenyl)-quinolin-2-one 38 g (0.127 mol) of 2-(2-methoxyphenyl)-3-(2-nitrophenyl)-2-propenoic acid are dissolved in 1 liter of methanol and hydrogenated under an $H_2$ pressure of 1 bar (5 hours) with the addition of 3 g of palladium-on-animal charcoal (5%). After the catalyst aas been filtered off with suction, the filtrate is concentrated and the residue is crystallized from isopropyl ether. 24.2 g of the title compound are obtained as colorless crystals of melting point 188°–190° C.

$^1$H-NMR (CDCl$_3$):δ=8.5 (broad s, 1H); 7.3–6.6 (m, 8H); 4.4–4.0 (X component of an ABX system, 1H); 3.8 (s, 3H); and 3.6–2.9 (AB component of an ABX system, 2H) ppm.

The following compounds were prepared in accordance with the instructions given in Example 1, using the corresponding starting materials:

EXAMPLE 2

1H-3,4-Dihydro-3(3-methoxyphenyl)-quinolin-2-one

Colorless crystals of melting point 138° C.

EXAMPLE 3

1H-3,4-Dihydro-3-(4-methoxyphenyl)-quinolin-2-one

Colorless crystals of melting point 190° C.

EXAMPLE 4

1H-3,4-Dihydroxy-1-methyl-3-(2-methoxyphenyl)-quinolin-2-one 3.09 g of sodium hydride (50% in oil) are washed with n-hexane and then suspended in 100 ml of dry dimethylformamide. 13.6 g (53.7 mmol) of 1H-3,4-dihydro-3-(2-methoxy-phenyl)-quinolin-2-one are added, while cooling with ice, and the mixture is stirred for 15 minutes. After addition of 9.14 g of iodomethane, the mixture is stirred for 1 hour, poured onto ice-water and extracted with ethyl acetate and the extract is washed five times with water, dried with sodium sulfate and concentrated. Trituration with diisopropyl ether gives 12.6 g of colorless crystals of melting point 111°–115° C.

The following compounds are likewise prepared in accordance with the instructions given in Example 4:

EXAMPLE 5

1H-3,4-Dihydro-1-methyl-3-(3-methoxyphenyl)-quinolin-2-one

Colorless crystals of melting point 84°–86° C.

EXAMPLE 6

1H-3,4-Dihydro-1-methyl-3-(4-methoxyphenyl)-quinolin-2-one

Colorless crystals of melting point 98°–99° C.

EXAMPLE 7

1H-3,4-Dihydro-1,3-dimethyl-3(2-methoxyphenyl)-quinolin-2-one 3.6 g of potassium hydride (50% in oil) are washed with n-hexane and suspended in 40 ml of dry dimethylformamide. 3 g (11.2 mmol) of 1H-3,4-dihydro-1-methyl-3-(2-methoxy-phenyl)-quinolin-2-one are added at 0° C., under nitrogen. After 15 minutes at 0° C., 3.18 g of iodomethane are added. After a further 2.5 hours at room temperature, the mixture is poured onto ice-water and extracted with ethyl acetate and the extract is washed with water, dried with sodium sulfate and concentrated. 3.3 g of the title compound are obtained.

$^1$H-NMR (CDCl$_3$):δ=7.3–6.6 (m, 8H); 3.85+2.55 (AB system, 2H); 3.69 (s, 3H); 3.43 (s, 3H); and 1.53 (s, 3H) ppm.

The following compounds were likewise prepared in accordance with the instructions given in Example 7, using suitable starting materials:

EXAMPLE 8

1H-3,4-Dihydro-3-ethyl-1-methyl-3-(2-methoxyphenyl)-quinolin-2-one

Colorless crystals of melting point 135°–137° C.

EXAMPLE 9

1H-3,4-Dihydro-3-isopropyl-1-methyl-3-(2-methoxyphenyl)-quinolin-2-one

Colorless oil.
$^1$H-NMR (CDCl$_3$):δ=7.1–6.5 (m, 8H); 3.6+3.05 (AB system, 2H); 3.72 (s, 3H), 3.39 (s, 3H); 2.65 (septet, 1H); and 1.05 and 1.0 (2d, 6H) ppm.

EXAMPLE 10

1H-3,4-Dihydro-3-n-hexyl-1-methyl-3-(2-methoxyphenyl)-quinolin-2-one

Colorless oil

EXAMPLE 11

1H-3,4-Dihydro-3-benzyl-1-methyl-3-(2-methoxyphenyl)-quinolin-2-one

Colorless oil.
$^1$H-NMR (CDCl$_3$):δ=7.2–6.5 (m, 13H); 3.73 (s, 3H); 3.36 (s, 3H); 3.77+2.74 (AB system, 2H); and 3.56 (AB system, 2H) ppm.

EXAMPLE 12

1H-3,4-Dihydro-3-isopropyl-1-methyl-3-(3-methoxyphenyl)-quinolin-2-one

Colorless oil.

EXAMPLE 13

1H-3,4-Dihydro-3-benzyl-1-methyl-3-(3-methoxyphenyl)-quinolin-2-one

Colorless oil.

EXAMPLE 14

1H-3,4-Dihydro-3-isopropyl-1-methyl-3-(4-methoxyphenyl)-quinolin-2-one

Colorless crystals

EXAMPLE 15

1H-3,4-Dihydro-3-benzyl-1-methyl-3-(4-methoxyphenyl)-quinolin-2-one

Colorless crystals

EXAMPLE 16

1H-3,4-Dihydro-1,3-dimethyl-3-(2-hydroxyphenyl)-quinolin-2-one 3.3 g (11.7 mmol) of 1H-3,4-dihydro-1,3-dimethyl-3-(2-methoxyphenyl)-quinolin-2-one are dissolved in 40 ml of dry methylene chloride, while cooling with ice, and 14 ml of a 1M solution of boron tribromide in n-hexane are added dropwise. After 3 hours at room temperature, the mixture is poured onto ice-water and extracted again with methylene chloride and the extract is dried with sodium sulfate. Crystallization from isopropanol/diisopropyl ether gives 2.18 g of the title compound as colorless crystals of melting point 162°–164° C.

The following compounds were prepared in accordance with instructions analogous to those given in Example 16, using the corresponding starting compounds:

EXAMPLE 17

1H-3,4-Dihydro-3-isopropyl-1-methyl-3(2-hydroxyphenyl)-quinolin-2-one

Colorless crystals of melting point 206°–208° C.

EXAMPLE 18

1H-3,4-Dihydro-3-ethyl-1-methyl-3-(2-hydroxyphenyl)-quinolin-2-one

Colorless crystals of melting point 171°–173° C.

EXAMPLE 19

1H-3,4-Dihydro-3-n-hexyl-1-methyl-3-(2-hydroxyphenyl)-quinolin-2-one

Colorless crystals of melting point 110°–111° C.

EXAMPLE 20

1H-3,4-Dihydro-3-benzyl-1-methyl-3-(2-hydroxyphenyl)-quinolin-2-one

Colorless crystals
$^1$H-NMR (CDCl$_3$):δ=9.35 (s, 1H); 7.3–6.5 (m, 13H): 3.75+3.1 (AB system, 2H); 3.40 (s, 3H); and 3.1 (s, 2H) ppm.

EXAMPLE 21

1H-3,4-Dihydro-3-isopropyl-1-methyl-3-(3-hydroxyphenyl)-quinolin-2-one

Colorless crystals

EXAMPLE 22

1H-3,4-Dihydro-3-benzyl-1-methyl-3-(3-hydroxyphenyl)-quinolin-2-one

Colorless crystals

EXAMPLE 23

1H-3,4-Dihydro-3-isopropyl-1-methyl-3-(4-hydroxyphenyl)-quinolin-2-one

Colorless crystals

EXAMPLE 24

1H-3,4-Dihydro-3-benzyl-1-methyl-3-(4-hydroxyphenyl)-quinolin-2-one

Colorless crystals

EXAMPLE 25

1H-3,4-Dihydro-1,3-dimethyl-3-[2-(4-bromobutoxy)-phenyl]-quinolin-2-one 2.2 g (8.2 mmol) of 1H-3,4-dihydro-1,3-dimethyl-3-(2-hydroxyphenyl)-quinolin-2-one, 1.57 g of potassium carbonate and 5.3 g of 1,4-dibromobutane are boiled under reflux in 30 ml of butan-2-one for 6 hours. After cooling, the salts are filtered off and the filtrate is concentrated. Trituration with diisopropyl ether gives 2.99 g of crystals of melting point 246°–249° C.

The following compounds are prepared in accordance with instructions analogous to those given in Example 25, using the corresponding starting materials:

EXAMPLE 26

1H-3,4-Dihydro-3-ethyl-1-methyl-3-[2-(4-bromobutoxy)-phenyl]-quinolin-2-one

Colorless oil.
$^1$H-NMR (CDCl$_3$): δ=7.3–6.6 (m, 8H); 4.2–3.8 (m, 2H); 3.8+2.7 (AB system, 2H); 3.55–3.2 (m+s, 5H); 2.3–1.6 (m, 6H); and 0.92 (t, 3H) ppm.

EXAMPLE 27

1H-3,4-Dihydro-3-n-hexyl-1-methyl-3-[2-(4-bromobutoxy)-phenyl]-quinolin-2-one

Colorless oil.
$^1$H-NMR (CDCl$_3$): $\delta = 7.2–6.6$ (m, 8H); 4.0 (t, 2H); 3.82+2.73 (AB system, 2H); 3.6–3.3 (s+m, 5H); 2.3–1.7 (m, 6H); 1.5–1.05 (m, 8H); and 0.85 (t, 3H) ppm.

EXAMPLE 28

1H-3,4-Dihydro-3-benzyl-1-methyl-3-[2-(4-bromobutoxy)-phenyl]-quinolin-2-one

Colorless crystals of melting point 122°–125° C.

EXAMPLE 29

1H-3,4-Dihydro-3-isopropyl-1-methyl-3-[2-(4-bromobutoxy)-phenyl]-quinolin-2-one

Colorless oil.
$^1$H-NMR (CDCl$_3$): $\delta = 7.1–6.5$ (m, 8H); 3.9 (m, 2H); 3.95+3.07 (AB system, 2H); 2.65 (septet, 1H); 2.3–1.8 (m, 4H); and 1.05 (d, 6H) ppm

EXAMPLE 30

1H-3,4-Dihydro-3-isopropyl-1-methyl-3-[2-(3-bromopropoxy)-phenyl]-quinolin-2-one Colorless oil

EXAMPLE 31

1H-3,4-Dihydro-3-isopropyl-1-methyl-3-[2-(5-bromopentoxy)-pheny]-quinolin-2-one

Colorless oil

EXAMPLE 32

1H-3,4-Dihydro-3-isopropyl-1-methyl-3-[3-(3-bromopropoxy)-phenyl]-quinolin-2-one Colorless oil

EXAMPLE 33

1H-3,4-Dihydro-3-isopropyl-1-methyl-3-[4-(3-bromopropoxy)-phenyl]-quinolin-2-one Colorless oil

EXAMPLE 34

1H-3,4-Dihydro-3-isopropyl-1-methyl-3-[3-(4-bromobutoxy)-phenyl]-quinolin-2-one

Colorless oil

EXAMPLE 35

1H-3,4-Dihydro-1-methyl-3-(2-hydroxyphenyl)-quinolin-2-one

Prepared in accordance with the instructions given in Example 16 from 1H-3,4-dihydro-1-methyl-3-(2-methoxy-phenyl)-quinolin-2-one and boron tribromide. Colorless crystals of melting point 160°–161° C.

EXAMPLE 36

1H-3,4-Dihydro-1-methyl-3-[2-(4-bromobutoxyphenyl)]-quinolin-2-one

Prepared in accordance with the process described in Example 25 from 1H-3,4-dihydro-1-methyl-3-(2-hydroxy-phenyl)-quinolin-2-one. Colorless oil.

EXAMPLE 37

1H-3,4-Dihydro-1-methyl-3-[2-[4-[4-[2-(3,4,5-trimethoxy-phenyl)-ethyl]-piperazinyl]-butoxy]-phenyl]-quinolin-2-one dihydrochloride 2.7g (5.6 mmol) of 1H-3,4-dihydro-1-methyl-3-[2-(4-bromo-butoxy)-phenyl]-quinolin-2-one, 3.5 g (11.2 mmol) of 2-(3,4,5-trimethoxyphenyl)-ethyl-piperazine and 3.5 g of potassium carbonate are boiled under reflux in 50 ml of isopropanol for 6 hours. After filtration, the filtrate is concentrated and the residue is chromatographed on silica gel with methylene chloride/methanol (20:1). 2.2 g of a colorless oil are obtained.
$^1$H-NMR (CDCl$_3$): $\delta = 7.3–6.7$ (m, 8H); 6.43 (s, 2H); 4.3–3.5 (m, 3H); 3.72+3.70 (2s, 9H); 3.43 (s, 3H); 3.5–3.0 (m, 2H); 2.9–2.2 (m, 14H); and 2.0–1.6 (m, 4H) ppm.

The free base is taken up in acetone, and an excess of 2.5 N ethanolic HCl is added. After concentration, the residue is taken up in acetone and filtered off with suction. 2.5 g of colorless crystals of melting point 228° C.

The following compounds are obtained in accordance with a process analogous to that described in Example 37, using the corresponding starting materials:

EXAMPLE 38

1H-3,4-Dihydro-1-methyl-3-isopropyl-3-[2-[4-[4-[2-(3,4,5-trimethoxyphenyl)-ethyl[-piperazinyl]-butoxy]-phenyl]-quinolin-2-one dihydrochloride Colorless crystals of melting point 236° C.
$^1$H-NMR (free base, CDCl$_3$): $\delta = 7.2–6.5$ (m, 8H) 6.41 (s, 2H); 4.1–3.9 (m, 2H); 3.83+ 3.81 (2s, 9H); 3.68+3.03 (AB system, J=15Hz, 2H); 3.37 (s, 3H); 2.9–2.4 (m, 15H); 2.0–1.5 (m, 4H); and 1.0 (d, 6H) ppm.

C$_{38}$H$_{53}$Cl$_2$N$_3$O$_5$ (702.77) Calculated C 64.9; H 7.5; N 6.0; Found C 64.6; H 7.6; N 5.7;

EXAMPLE 39

1H-3,4-Dihydro-1-methyl-3-benzyl-3-[2-[4-[4-[2-(3,4,5-tri-methoxypheny -ethyl]-piperazinyl]-butoxy]-phenyl]-quino-lin-2-one dihydrochloride Colorless crystals of melting point 210° C. (decomposition) $^1$H-NMR (free base, CDCl$_3$): $\delta = 7.2–6.5$ (m, 13H); 6.40 (s, 2H); 3.71+3.69 (2s, 9H); 4.2–3.6 (m, 3H); 3.80+3.20 (AB system, =14 Hz, 2H); 3.4 (s, 3H), 3.0–2.2 (m, 15H); and 2.0–1.6 (m, 4H) ppm.

C$_{42}$H$_{51}$N$_3$O$_5$.2HCl.H$_2$O (768.33) Calculated C 65.6; H 7.2; N 5.5. Found C 65.8; H 7.1; N 5.4.

EXAMPLE 40

1H-3,4-Dihydro-1-methyl-3-ethyl-3-[2-[4-[4-[2-(3,4,5-tri-methoxyphenyl -piperazinyl]-butoxy]-phenyl]-quino-lin-2-one dihydrochloride Colorless crystals of melting point 235°–237° C.
$^1$H-NMR (free base, CDCl$_3$): $\delta = 7.3–6.8$ (m, 8H); 6.42 (s, 2H), 4.0–3.8 (m, 2H); 3.85+3.82 (2s, 9H); 3.8+2.7 (AB system, J=15Hz, 2H); 3.42 (s, 3H); 2.8–2.3 (m, 14H); 3.04 (2q, 2H); 1.8–1.6 (m, 4H); and 0.94 (t, 3H) ppm.

C$_{37}$H$_{49}$N$_3$O$_5$×2HCl (688.74) Calculated C 64.5; H 7.4; N 6.1. Found C 64.4; H 7.4; N 6.1.

EXAMPLE 41

1H-3,4-Dihydro-1-methyl-3-n-hexyl-3-[2-[4-[4-[2-(3,4,5-trimethoxyphenyl-ethyl)]-piperazinyl]-butoxy]-phenyl]-quinolin-2-one dihydrochloride Colorless crystals of melting point 235°–237° C.
$^1$H-NMR (free base, CDCl$_3$): δ=7.2–6.6 (m, 8H); 6.4 (s, 2H); 4.3–3.6 (m, 3H); 3.82 (s, 9H); 3.40 (s, 3H); 2.9–2.2 (m, 15H); 2.2–1.5 (m, 6H); 1.4–1.0 (m, 8H); and 0.83 (t, 3H) ppm C$_{41}$H$_{57}$N$_3$O$_5$×2HCl (744.83) Calculated C 66.1;, H 7.9; N 5.6; Found C 66.5; H 8.0; N 5.5.

EXAMPLE 42

1H-3,4-Dihydro-1,3-dimethyl-3-[2-[4-[4-[2-(3,4,5-trimethoxyphenyl)
-ethyl]-piperazinyl]-butoxy]-phenyl]-quinolin-2-one dihydrochloride Colorless crystals of melting point 252°–254° C.
$^1$H-NMR (free base, CDCl$_3$): δ=7.3–6.6 (m, 8H); 6.4 (s, 2H); 4.1–3.6 (m, 3H); 3.82 (s, 9H); 3.40 (s, 3H); 2.7–2.1 (m, 15H); 200–1.5 (m, 4H); and 1.50 (s, 3H) ppm.

C$_{36}$H$_{47}$N$_3$O$_5$×2 HCl (674.72) Calculated C 64.1; H 7.3; N 6.2; Found C 64.3; H 7.5; N 6.0.

EXAMPLE 43

1H-3,4-Dihydro-1,3-dimethyl-3-[2-[4-[N-methyl-N-(2-(3,4-dimethoxyphenyl)
-ethyl)-amino]-butoxy]-phenyl]-quinolin2-one hydrochloride Colorless crystals of melting point 107° C. (decomposition)
$^1$H-NMR (free base, CDCl$_3$): δ=7.3–6.6 (m, 11H); 4.2–3.6 (m, 3H); 3.76 (s, 6H); 3.30 (s, 3H); 2.6–2.2 (m, 6H); 2.13 (s, 3H); 1.8–1.5 (m, 4H); and 1.44 (s, 3H) ppm.

C$_{32}$H$_{40}$N$_2$O$_4$×HCl×2H$_2$O (589.18) Calculated C 65.2; H 7.7; N 4.6; Found C 65.2; H 7.5; N 4.5.

The compounds of the following examples are prepared in accordance with a process analogous to that described in Example 37, but the free base is in each case dissolved in acetone, and equivalent amounts of oxalic acid are added. After concentration, the residue is crystallized with ethyl acetate/ether.

EXAMPLE 44

1H-3,4-Dihydro-3-ethyl-1-methyl-3-[2-[4-[N-methyl-N-[2(3,4-dimethoxyphenyl)-ethyl]-amino]-butoxy]-phenyl]-quinolin-2-one oxalate Colorless crystals of melting point 120° C.
$^1$H-NMR (free base, CDCl$_3$): δ=7.2–6.6 (m, 11H); 4.1–3.5 (m, 3H); 3.86 (s, 6H); 3.40 (s, 3H); 3.0–2.5 (m, 7H); 2.30 (s, 3H); 2.3–1.6 (m, 6H); and 0.93 (t, 3H) ppm C$_{33}$H$_{42}$N$_2$4×C$_2$H$_2$O$_4$ (620.75) Calculated C 67.7; H 7.1; N 4.5; Found C 67.5; H 7.2; N 4.4.

EXAMPLE 45

1H-3,4-Dihydro-3-n-hexyl-1-methyl-3-[2-[4-[N-methyl-N-[2-(3,4-dimethoxyphenyl)-ethyl]-amino]-butoxy]-phenyl]-quinolin-2-one oxalate Colorless amorphous powder
$^1$H-NMR (free base, CDCl$_3$): δ=7.2–6.6 (m, 11H); 4.0–3.6 (m, 3H); 3.82 (s, 6H); 3.40 (s, 3H); 2.8–2.4 (m, 7H); 2.27 (s, 3H); 2.1–1.5 (m, 6H); 1.5–1.0 (m, 6H); and 0.83 (t, 3H) ppm.

C$_{37}$H$_{50}$N$_2$O$_4$×C$_2$H$_2$O$_4$×H$_2$O (694.88) Calculated C 67.4; H 7.8; N 4.0; Found C 67.4; H 7.7; N 3.9.

EXAMPLE 46

1H-3,4-Dihydro-3-benzyl-1-methyl-3-[2-[4-[N-methyl-N-[2-(3,4-dimethoxyphenyl)-ethyl]-amino]-butoxy]-phenyl]-quinolin-2-one oxalate Colorless crystals of melting point 155° C.
$^1$H-NMR (free base, CDCl$_3$): δ=7.1–6.6 (m, 16H); 4.1–3.7 m, 3H); 3.82 (s, 6H); 3.53+3.38 (AB system, 2H); 3.32 (s, 3H); 3.0–2.5 (m, 7H); 2.43 (s, 3H); and 2.1–1.6 (m, 4H) ppm.

C$_{38}$H$_{44}$N$_2$O$_4$×C$_2$H$_2$O$_4$ (682.82)
Calculated C 70.4; H 6.7; N 4.1; Found C 70.1; H 6.8; N 4.1.

EXAMPLE 47

1H-3,4-Dihydro-3-isopropyl-1-methyl-3-[2-[4-[N-methyl-N-[2-3,4-dimethoxyphenyl)-ethyl]-amino]-butoxy]-phenyl]-quinolin-2-one oxalate Colorless amorphous powder
$^1$H-NMR (free base, CDCl$_3$): δ=7.1–6.6 (m, 11H); 4.1–3.6 (m, 3H); 3.8 (s, 6H); 3.4 (s, 3H); 3.0–2.3 (m, 8H); 2.4 (s, 2H); 2.1–1.6 (m, 4H); and 1.1+0.9 (2d, 6H) ppm.

EXAMPLE 48

1H-3,4-Dihydro-3-benzyl-1-methyl-3-[2-[4-[4-[4,4-bis-(4-fluorophenyl)
-butyl]-piperazinyl]-butoxy]-phenyl]-quinolin-2-one dihydrochloride Prepared in accordance with instructions analogous to those given in EXAMPLE 37, from equivalent amounts of 1H-3,4-dihydro-3-benzyl-1-methyl-3-[2-(4-bromobutoxy)-phenyl]-quinolin-2-one and 1-[4,4-bis-(4-fluorophenyl)-butyl]-piperazine.

Colorless crystals of melting point 155° C. (decomposition)
$^1$H-NMR (free base, CDCl$_3$): δ=7.3–6.5 (m, 21H); 4.2–3.9 (m, 3H); 3.82+2.77 (AB system, J=14H, 2H); 3.63+3.35 (AB system, J=13H, 2H); 2.6–2.2 (m, 14H); and 2.2–1.2 (m, 8H) ppm.

C$_{47}$H$_{51}$F$_2$N$_3$O$_2$×2HCl×H$_2$O (818.88) Calculated C 68.9; H 6.8; N 5.1; Found C 69.2; H 6.9; N 5.2.

The compounds of the following examples are prepared in accordance with the process described in EXAMPLE 48, from the corresponding starting materials, but 2.1 equivalents of maleic acid are added to the free bases in acetone solution.

EXAMPLE 49

1H-3,4-Dihydro-1,3-dimethyl-3-[2-[4-[4-[4,4-bis-(4-fluorophenyl)
-butyl]-piperazinyl]-butoxy]-phenyl]-quinolin-2-one bis-maleate Colorless crystals of melting point 169°–171° C. (decomposition)
$^1$H-NMR (free base, CDCl$_3$): δ=7.3–6.6 (m, 16H); 4.1–3.9 (m, 3H); 3.82+2.57 (AB system, J=10Hz, 2H); 3.40 (s, 3H); 2.5–2.0 (m, 14H); 2.0–1.3 (m, 8H); and 1.50 (s, 3H) ppm.

C$_{41}$H$_{47}$F$_2$N$_3$O$_2$×2C$_4$H$_4$O$_4$ (884.00) Calculated C 66.6; H 6.3; r N 4.8; Found C 66.5; H 6.3; N 4.8.

EXAMPLE 50

1H-3,4-Dihydro-3-ethyl-1-methyl-3-[2-[4-[4-[4,4-bis-(4-fluorophenyl)-butyl]-piperazinyl]-butoxy]-phenyl]-quinolin2-one bis-maleate Colorless crystals of melting point 169°–171° C.

$^1$H-NMR (free base, CDCl$_3$): δ=7.3–6.6 (m, 16H); 4.2–3.6 (m, 4H); 3.38 (s, 3H); 2.85–2.1 (m, 15H); 2.05 (q, 2H); 2.0–1.4 (m, 8H); and 0.93 (t, 3H) ppm $C_{42}H_{49}F_2N_3O_2 \times 2C_4H_4O_4$ (898.02) Calculated C 66.9; H 6.4; N 4.7; Found C 66.7; H 6.71 N 4.3.

EXAMPLE 51

1H-3,4-Dihydro-3-n-hexyl-1-methyl-3-[2-[4-[4-[4,4-bis-(4-fluorophenyl)-butyl]-piperazinyl]-phenyl]-quinolin-2-one bis-maleate Colorless crystals of melting point 176°–178° C.

$^1$H-NMR (free base, CDCl$_3$): δ=7.4–6.6 (m, 16H); 4.2–3.6 (m, 4H); 3.39 (s, 3H); 2.85–2.2 (m, 14H); 2.1–1.4 (m, 10H); 1.5–1.15 (m, 8H); and 0.85 (t, 3H) ppm $C_{46}H_{57}F_2N_3O_2 \times 2C_4H_4O_4$ (954.13) Calculated C 68.0; H 6.8; N 4.4; Found C 67.9; H 6.9; N 4.2.

The compounds listed in the following table are prepared in accordance with the instructions given in the preceding examples, from the corresponding starting materials.

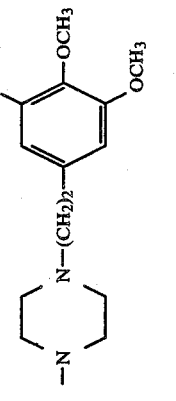
| Example No. | R(1) | R(2) | R(3) | R(4) | m | R(6) | Side chain in position | NMR (δ, ppm) |
|---|---|---|---|---|---|---|---|---|
| 52 | H | CH₃ | CH(CH₃)₂ | H | 4 | 3,4,5-tri(OCH₃)-phenyl-piperazinyl | 3' | 7.3–6.6(m,8H);6.41(s,2H); 4.1–3.9(m,2H);3.8+3.75 (2s,9H);3.7–3.0(m,2H); 3.4(s,3H);2.9–2.4(m,15H); 2.0–1.5(m,4H);1.0(d,6H) |
| 53 | H | CH₃ | CH(CH₃)₂ | H | 3 | 3,4,5-tri(OCH₃)-phenyl-piperazinyl | 3' | 7.3–6.6(m,8H);6.4(s,2H); 4.1–3.9(m,2H);3.85+3.82(2s,9H); 3.7–3.0(m,2H);3.4(s,3H); 2.9–2.4(m,15H);2.0–1.6(m,2H); 1.0(d,6H) |
| 54 | H | CH₃ | CH(CH₃)₂ | H | 3 | 3,4-di(OCH₃)-phenyl-N(CH₃)CH₂CH₂- | 3' | 7.1–6.6(m,11H);4.1–3.8 (m,3H);3.8(s,6H);3.4(s,3H); 3.0–2.3(m,9H);2.1(s,3H); 2.1–1.7(m,2H);1.0(d,6H) |
| 55 | H | CH₃ | CH(CH₃)₂ | H | 3 | 3,5-di(OCH₃)-phenyl-piperidinyl | 3' | 7.3–6.5(m,11H);4.1–3.9 (m,2H);3.7(s,6H);3.7–3.0 (m,2H);3.4(s,3H)2.9–2.4 (m,15H);2.0–1.6(m,2H);1.0 (d,6H) |

-continued
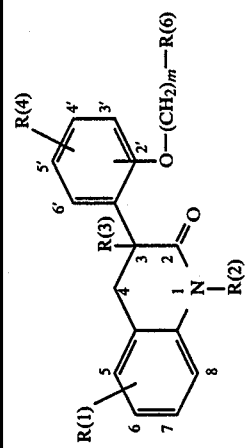
| Example No. | R(1) | R(2) | R(3) | R(4) | m | R(6) | Side chain in position | NMR (δ, ppm) |
|---|---|---|---|---|---|---|---|---|
| 56 | H | $CH_3$ | $CH_2C_6H_5$ | H | 3 | piperidine-$N-(CH_2)_2$-(3,4,5-tri-$OCH_3$)phenyl | 3' | 7.2–6.5(m,13H);6.4(s,2H); 3.7(s,9H);4.2–3.2(m,5H); 3.0–2.2(m,15H);2.0–1.7 (m,2H) |
| 57 | H | $CH_3$ | $n-C_6H_{13}$ | H | 3 | piperidine-$N-(CH_2)_2$-(3,4,5-tri-$OCH_3$)phenyl | 3' | 7.2–6.6(m,8H);6.4(s,2H) 4.2–3.6(m,3H);3.8(2s,9H); 3.4(s,3H);2.9–2.2(m,15H); 2.2–1.5(m,4H);1.4–1.0 (m,8H);0,85(t,3H) |
| 58 | H | H | $CH(CH_3)_2$ | H | 4 | piperidine-$N-(CH_2)_2$-(3,4,5-tri-$OCH_3$)phenyl | 2' | 7.2–6.5(m,8H);6.4(s,2H); 4.1–3.9(m,2H);3.85(s,9H); 2.9–2.4 (m,15H);2.0–1.5(m,4H); 1.0(d,6H) |
| 59 | H | $CH_3$ | $CH(CH_3)_2$ | H | 4 | piperidine-$N-CO-CH_2$-(3,4,5-tri-$OCH_3$)phenyl | 2' | 7.2–6.5(m,8H);6.5(s,2H); 4.1–3.9(m,2H);3.9(s,9H); 3.8(s,2H);3.7–3.0(m,2H); 3.4(s,3H);2.9–2.4(m,11H); 2.0–1.5(m,4H);1.0(d,6H) |

-continued

| Example No. | R(1) | R(2) | R(3) | R(4) | m | R(6) | Side chain in position | NMR (δ, ppm) |
|---|---|---|---|---|---|---|---|---|
| 60 | H | CH₃ | n-C₆H₁₃ | H | 4 | piperazine-N-CO-CH₂-(3,4,5-trimethoxyphenyl) | 2' | 7.2–6.6(m,8H);6.5(s,2H); 4.1–3.6(m,3H);3.9(s,9H); 3.8(s,2H);3.4(s,3H);2.9–2.2(m,11H);2.2–1.5(m,6H); 1.4–1.0(m,8H);0.85(t,3H) |
| 61 | H | CH₃ | cyclohexyl | H | 4 | piperazine-N-(CH₂)₂-(3,4,5-trimethoxyphenyl) | 2' | 7.2–6.6(m,8H);6.5(s,2H); 4.1–3.9(m,2H);3.85(s,9H); 3.7–3.0(m,2H);3.4(s,3H); 2.9–2.3(m,15H);2.2–1.3 (m,16H) |
| 62 | H | CH₃ | CH₂-cyclohexyl | H | 4 | piperazine-N-(CH₂)₂-(3,4,5-trimethoxyphenyl) | 2' | 7.2–6.6(m,8H);6.5(s,2H); 4.1–3.9(m,2H);3.85(s,9H); 3.7–3.0(m,2H);3.4(s,3H); 2.9–2.3(m,15H);2.2–1.3 (m,16H) |
| 63 | H | CH₃ | (CH₃)₂CH | H | 2 | piperazine-N-(CH₂)₂-(3,4,5-trimethoxyphenyl) | 4' | 7.2–6.5(m,8H);6.5(s,2H); 4.1–3.9(m,2H);3.8(s,9H); 3.7–3.0(m,2H);3.4(s,3H); 2.9–2.4(m,15H);1.0(d,6H) |

-continued
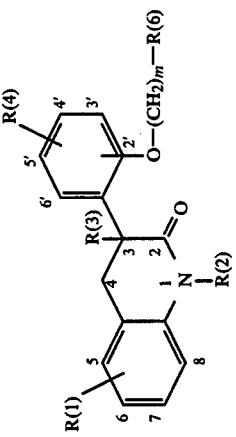
| Example No. | R(1) | R(2) | R(3) | R(4) | m | R(6) | Side chain in position | NMR (δ, ppm) |
|---|---|---|---|---|---|---|---|---|
| 64 | H | CH₃ | (CH₃)₂CH | H | 3 | 3,4,5-tri-OCH₃-phenyl-CH₂-N(piperidine) | 4' | 7.2–6.5(m,8H);6.50s,2H); 4.2–3.9(m,2H);3.85(s,9H); 3.75–3.05(m,2H);3.38(s,3H); 2.9–2.4(m,15H);2.0–1.6 (m,2H);1.0(d,6H) |
| 65 | H | CH₃ | (CH₃)₂CH | H | 4 | 3,4,5-tri-OCH₃-phenyl-CH₂-N(piperidine) | 4' | 7.2–6.5(m,8H);6.4(s,2H); 4.2–3.8(m,2H);3.85(s,9H); 3.7–3.0(m,2H);3.4(s,3H); 2.9–2.4(m,15H);2.0–1.5 (m,4H);1.0(d,6H) |
| 66 | H | CH₃ | n-C₆H₁₃ | H | 3 | 3,4,5-tri-OCH₃-phenyl-CH₂-N(piperidine) | 4' | 7.2–6.5(m,8H);6.4(s,2H); 4.3–3.9(m,2H);3.85(s,9H); 3.7–3.0(m,2H);3.4(s,3H); 2.9–2.2(m,15H);2.2–1.5 (m,4H);1.4–1.0(m,8H); 0.85(t,3H) |
| 67 | H | CH₃ | CH₃ | H | 3 | 3,4,5-tri-OCH₃-phenyl-CH₂-N(piperidine) | 3' | 7.3–6.6(m,8H);6.4(s,2H); 4.1–3.6(m,2H);3.82(s,9H); 3.4(s,3H);2.7–2.11(m,15H); 2.0–1.5(m,2H);1.5(s,3H) |

-continued

| Example No. | R(1) | R(2) | R(3) | R(4) | m | R(6) | Side chain in position | NMR (δ, ppm) |
|---|---|---|---|---|---|---|---|---|
| 68 | 6-Cl | CH₃ | (CH₃)₂CH | H | 4 | 3,4,5-tri(OCH₃)-phenyl-piperazinyl-N-(CH₂)₂- | 2' | 7.3–6.6(m,7H);6.4(s,2H); 4.1–3.9(m,2H);3.85(s,9H); 3.7–3.0(m,2H);3.4(s,3H); 2.9–2.4(m,15H);2.0–1.5 (m,4H);1.0(d,6H) |
| 69 | 6-CH₃ | CH₃ | (CH₃)₂CH | H | 4 | 3,4,5-tri(OCH₃)-phenyl-piperazinyl-N-(CH₂)₂- | 2' | 7.3–6.6(m,7H);6.4(s,2H); 4.1–3.9(m,2H);3.85(s,9H); 3.7–3.1(m,2H);3.4(s,3H); 2.9–2.4(m,15H);2.3(s,3H); 2.0–1.5(m,4H)1.0(d,6H) |
| 70 | 6-OCH₃ | CH₃ | (CH₃)₂CH | H | 4 | 3,4,5-tri(OCH₃)-phenyl-piperazinyl-N-(CH₂)₂- | 2' | 7.3–6.5(m,7H);6.4(s,2H); 4.1–3.9(m,2H);3.9–3.75 (3s,12H);3.7–3.1(m,2H);3.4(s,3H); 2.9–2.4(m,15H);2.0–1.5 (m,4H);1.0(d,6H) |
| 71 | 6,7-(OCH₃)₂ | CH₃ | (CH₃)₂CH | H | 4 | 3,4,5-tri(OCH₃)-phenyl-piperazinyl-N-(CH₂)₂- | 2' | 7.1–6.5(m,6H);6.4(s,2H); 4.1–3.9(m,2H);3.9–3.7 (3s,15H);3.7–3.0(m,2H);3.4 (s,3H);2.9–2.4(m,15H);2.0–1.5 (m,4H);1.0(d,6H) |

-continued
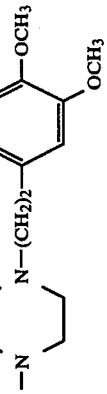
| Example No. | R(1) | R(2) | R(3) | R(4) | m | R(6) | Side chain in position | NMR (δ, ppm) |
|---|---|---|---|---|---|---|---|---|
| 72 | 6,7-OCH$_2$O | CH$_3$ | (CH$_3$)$_2$CH | H | 4 | 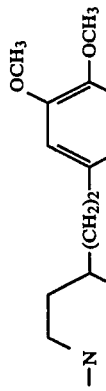 | 2' | 7.1–6.5(m,6H);6.4(s,2H); 5.8(s,2H);4.1–3.9(m,2H); 3.85(s,9H);3.7–3.0(m,2H); 3.4(s,3H);2.9–2.4(m,15H); 2.0–1.5(m,4H);1.0(d,6H) |
| 73 | H | CH$_3$ | (CH$_3$)$_2$CH | H | 4 | | 2' | 7.2–6.5(m,8H);6.4(s,2H); 4.1–3.9(m,2H);3.8(s,9H);3.4(s,3H); 2.9–2.4(m,10H);2.0–1.5 (m,10H);1.0(d,6H) |
| 74 | H | CH$_3$ | (CH$_3$)$_2$CH | 5'-Cl | 4 | 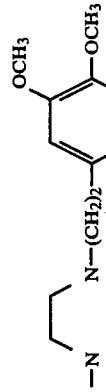 | 2' | 7.2–6.5(m,7H);6.4(s,2H); 4.1–3.9(m,2H);3.85(s,9H); 3.4(s,3H); 2.9–2.4(m,15H);2.0–1.5 (m,4H);1.0(d,6H) |
| 75 | 6-Cl | CH$_3$ | n-C$_6$H$_{13}$ | H | 4 | 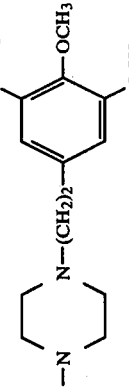 | 2' | 7.2–6.5(m,7H);6.4(s,2H); 4.1–3.9(m,2H);3.85(s,9H); 3.7–3.0(m,3H);3.4(s,3H); 2.9–2.4(m,15H);2.0–1.5 (m,6H);1.4–1.0(m,8H); 0.85(t,3H) |

-continued

Structural formula showing a quinolinone-type scaffold with substituents R(1) at positions 5-8 of a benzene ring fused to an N-containing ring (N-R(2)), with R(3) at position 3, C=O at position 2, and a CH2 linker at position 4 to a phenyl ring bearing R(4) and an O—(CH2)$_m$—R(6) side chain at position 2'.

| Example No. | R(1) | R(2) | R(3) | R(4) | m | R(6) | Side chain in position | NMR (δ, ppm) |
|---|---|---|---|---|---|---|---|---|
| 76 | 6-Cl | CH$_3$ | C$_6$H$_5$CH$_2$ | H | 4 | piperazinyl-N—(CH$_2$)$_2$—(3,4,5-trimethoxyphenyl) (OCH$_3$, OCH$_3$, OCH$_3$) | 2' | 7.2–6.5(m,7H);6.4(s,2H); 4.2–3.6(m,3H);3.8(s,9H); 3.8–3.2(m,2H);3.4(s,3H); 3.0–2.2(m,15H);2.0–1.6 (m,4H) |
| 77 | H | CH$_3$ | (CH$_3$)$_2$CH | H | 5 | piperazinyl-N—(CH$_2$)$_2$—(3,4,5-trimethoxyphenyl) (OCH$_3$, OCH$_3$, OCH$_3$) | 2' | 7.2–6.5(m,8H);6.4(s,2H); 4.1–3.9(m,2H);3.8(s,9H); 3.7–3.0(m,2H);3.4(s,3H); 2.9–2.4(m,15H);2.0–1.5 (m,8H);1.0(d,6H) |
| 78 | 6-Cl | CH$_3$ | (CH$_3$)$_2$CH | H | 4 | piperazinyl-N—(CH$_2$)$_3$—CH(4-F-C$_6$H$_4$)$_2$ | 2' | 7.3–6.6(m,15H);4.1–3.9(m,3H); 3.8–2.8(m,2H);3.4(s,3H); 2.5–2.0(m,15H);2.0–1.3 (m,8H);1.0(d,6H) |
| 79 | 6-CH$_3$ | CH$_3$ | (CH$_3$)$_2$CH | H | 4 | piperazinyl-N—(CH$_2$)$_3$—CH(4-F-C$_6$H$_4$)$_2$ | 2' | 7.3–6.6(m,15H);4.1–3.9(m,3H); 3.8–2.9(m,2H);3.4(s,3H); 2.5–2.0(m,15H);2.3(s,3H); 2.0–1.3(m,8H);1.0(d,6H) |

-continued
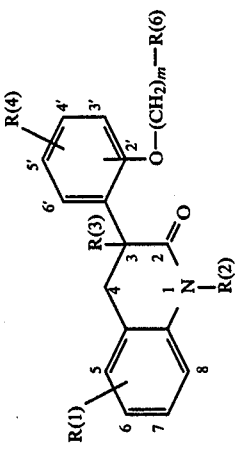
| Example No. | R(1) | R(2) | R(3) | R(4) | m | R(6) | Side chain in position | NMR (δ, ppm) |
|---|---|---|---|---|---|---|---|---|
| 80 | 6-OCH$_3$ | CH$_3$ | (CH$_3$)$_2$CH | H | 4 | −N((CH$_2$)$_3$−CH(−C$_6$H$_4$F)$_2$)piperidine | 2' | 7.3–6.6(m,15H);4.1–3.9(m,3H); 3.8–2.9(m,2H);3.8(s,3H); 3.4(s,3H);2.5–2.0(m,15H);2.0–1.3 (m,8H);1.0(d,6H) |
| 81 | H | CH$_3$ | (CH$_3$)$_2$CH | H | 3 | −N(CH$_3$)(CH$_2$)$_2$−C$_6$H$_3$(OCH$_3$)$_2$ | 2' | 7.1–6.6(m,11H);4.1–3.8(m,3H); 3.8(s,6H);3.4(s,3H);3.0–2.3 (m,9H);2.4(s,3H);2.2–1.7(m,2H); 1.0(d,6H) |

EXAMPLE 82

1H-3,4-Dihydro-3-isopropyl-1-methyl-3-[2-[2-hydroxy-3-[4-([2-(3,4,5-trimethoxyphenyl)-ethyl]-piperazinyl]-propoxy]phenyl]-quinolin-2-one dihydrochloride (a)

1H-3,4-Dihydro-3-isopropyl-1-methyl-3-[2-(2,3-epoxypropoxy)-phenyl]-quinolin-2-one Prepared from the compound from EXAMPLE 17 and epichlorohydrin and potassium carbonate in accordance with instructions analogous to those given in EXAMPLE 25. Colorless oil $^1$H-NMR (CDCl$_3$): δ=7.3–6.6 (m, 8H); 5.0–4.0 (m, 2H); 3.8–3.0 (m, 3H); 3.4 (s, 3H); and 1.0 (d, 6H)

(b)

1H-3,4-Dihydro-3-isopropyl-1-methyl-3-[2-[2-hydroxy-3-[4-[2-(3,4,5-trimethoxyphenyl)-ethyl]-piperazinyl]-propoxy]-phenyl]-quinolin-2-one dihydrochloride In each case 5 mmol of the epoxide from a) and 2-(3,4,5-trimethoxyphenyl) ethyl-piperazine are warmed to 80° C. in toluene. After cooling, the mixture is concentrated and the residue is chromatographed on silica gel with methylene chloride/methanol (10:1) as the mobile phase. Colorless oil $^1$H-NMR (CDCl$_3$): δ=7.3–6.6 (m, 8H); 6.4 (s, 2H); 4.4–4.1 (m, 2H); 4.0–3.0 (m, 3H); 3.85 (s, 9H); 3.4 (s, 3H); 3.0–2.4 (m, 15H); and 1.0 (d, 6H)

The free base is converted into the hydrochloride with ethanolic HCl; colorless crystals.

The following compounds are obtained in accordance with a process analogous to that described in EXAMPLE 82, using suitable starting materials:

EXAMPLE 83

1H-3,4-Dihydro-3-n-hexyl-1-methyl-3-[2-[2-hydroxy-3-[4-[2-3,4,5-trimethoxyphenyl)-ethyl]-piperazinyl]-propoxy]phenyl]-quinolin-2-one dihydrochloride Colorless crystals $^1$H-NMR (free base, CDCl$_3$) : δ=7.2–6.6 (m, 8H) 6.4 (s, 2H); 4.0–3.0 (m, 3H); 3.85 (s, 9H); 3.4 (s, 3H); 3.1–2.2 (m, 14H); 2.2–1.5 (m, 2H); 1.4–1.0 (m, 8H); and 0.83 (t, 3H)

EXAMPLE 84

1H-3,4-Dihydro-3-benzyl-1-methyl-3-[2-[2-hydroxy-3-[4-[2-(3,4,5-trimethoxyphenyl)-ethyl]piperazinyl]-propoxy]phenyl-]-quinolin-2-one dihydrochloride Colorless crystals $^1$H-NMR (free base, CDCl$_3$): δ=7.2–6.6 (m, 13H); 6.4 (s, 2H); 4.4–4.1 (m, 2H); 4.0–2.8 (m, 5H); 3.85 (s, 9H); 3.4 (s, 3H); and 3.1–2.2 (m, 15H).

EXAMPLE 85

1H-3,4-Dihydro-3-isopropyl-1-methyl-3-[2-[2-hydroxy-3-[N-methyl-N-[2-(3,4-dimethoxyphenyl)-ethyl]-amino]-propoxy]phenyl]-quinolin-2-one hydrochloride Colorless crystals $^1$H-NMR (free base, CDCl$_3$): δ=7.3–6.6 (m, 11H); 4.4–3.6 (m, 3H); 3.8 (s, 6H); 3.3 (s, 3H); 3.7–3.3 (m, 1H); 2.6–2.2 (m, 7H); 2.2 (s, 3H); and 1.0 (d, 6H)

We claim:

1. A compound of the formula I

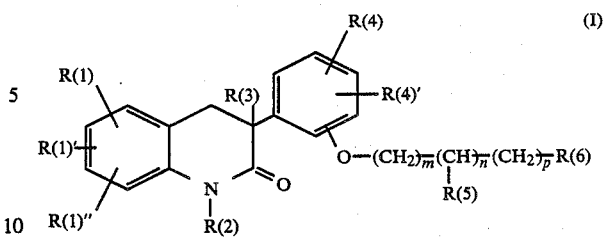

in which

R(1), R(1)' and R(1)" are identical or different and independent of one another and denote hydrogen, (C$_1$–C$_4$)-alkyl, (C$_1$–C$_3$)-alkoxy, F, Cl, CF$_3$, nitro, hydroxyl, acetamido or amino, or R(1) and R(1)' together denote (C$_1$–C$_2$)-alkylenedioxy, R(2) denotes hydrogen, straight-chain or branched (C$_1$–C$_{10}$)-alkyl or straight-chain or branched (C$_3$–C$_{10}$)-alkenyl, R(3) denotes hydrogen, straight-chain or branched (C$_1$–C$_{10}$)-alkyl, straight-chain or branched (C$_3$–C$_{10}$)-alkenyl, (C$_4$–C$_8$)-cycloalkyl, (C$_4$–C$_8$)-cycloalkyl-(C$_1$–C$_4$)-alkyl or phenyl-(C$_1$–C$_4$)-alkyl, the phenyl radical being unsubstituted or substituted by one, two or three substituents from the group consisting of (C$_1$–C$_4$)-alkyl, (C$_1$–C$_3$)-alkoxy, F, Cl, CF$_3$, (C$_1$–C$_2$)-alkylenedioxy and nitro, R(4) and R(4)' are identical or different and independently of one another denote hydrogen, (C$_1$–C$_4$)-alkyl, (C$_1$–C$_3$)-alkoxy, F, Cl, CF$_3$, nitro, hydroxyl, acetamido or amino, R(5) denotes hydrogen, hydroxyl or (C$_1$–C$_3$)-alkyl, m denotes 1, 2, 3 or 4, n denotes 0 or 1, p denotes 0, 1, 2, 3 or 4 and R(6) denotes one of the following groups

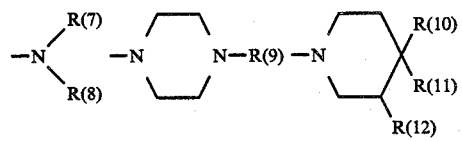

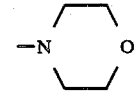

in which

R(7) and R(8) are identical or different and independently of one another denote hydrogen, (C$_1$–C$_{10}$)-alkyl, (C$_4$–C$_8$)-cycloalkyl, (C$_4$–C$_8$)-cycloalkyl-(C$_1$–C$_4$)-alkyl, phenyl-(C$_1$–C$_6$)-alkyl, the phenyl radical being unsubstituted or substituted by one, two or three radicals from the group consisting of (C$_1$–C$_4$)-alkylenedioxy, F, Cl, CF$_3$ and hydroxyl, or pyridyl-C$_1$–C$_4$)-alkyl, R(9) denotes hydrogen, straight-chain or branched (C$_1$–C$_{10}$)-alkyl, phenyl, phenyl-(C$_1$–C$_4$)-alkyl or diphenyl-(C$_1$–C$_5$)-alkyl, phenyl-(C$_1$–C$_4$)-alkanoyl, benzoyl, the phenyl radical in each case being unsubstituted or substituted by one, two or three radicals from the group consisting of (C$_1$–C$_4$)-alkyl, (C$_1$–C$_4$)-alkoxy, (C$_1$–C$_2$)-alkylenedioxy, F, Cl, CF$_3$ and hydroxyl, or pyridyl, pyrimidinyl or (C$_1$–C$_5$)-alkanoyl, R(10) denotes hydrogen, $(C_1-C_{10})$-alkyl, phenyl, phenyl-$(C_1-C_4)$-alkyl, the phenyl radical in each case being unsubstituted or substituted by one, two or three radicals from the group consisting of $(C_1-C_4)$-alkyl, $(C_1-C_4)$-alkoxy, $(C_1-C_2)$-alkylenedioxy, F, Cl and hydroxyl, R(11) denotes hydrogen, hydroxyl or $(C_1-C_4)$-alkoxy, or together with R(12) denotes a bond, and R(12) denotes hydrogen, or together with R(11) denotes a bond;

and the salts of the compounds of the formula I with pharmaceutically acceptable acids.

2. A compound I as claimed in claim 1, wherein

R(1) and R(1)' are identical or different and independently of one another denote hydrogen, methyl, ethyl, methoxy, ethoxy, fluorine, chlorine, $CF_3$, nitro or acetamido;

R(1)'' denotes hydrogen, p1 R(2) denotes hydrogen or straight-chain or branched $(C_1-C_6)$-alkyl, R(3) denotes hydrogen, straight-chain or branched $(C_1-C_6)$-alkyl, allyl, cyclopentyl, cyclohexyl, benzyl or phenethyl, in each case unsubstituted or substituted by $(C_1-C_3)$-alkyl, $(C_1-C_3)$-alkoxy, F, Cl, $CF_3$, $(C_1-C_2)$-alkylenedioxy or nitro, R(4) denotes hydrogen, methyl, methoxy, ethoxy, chlorine, nitro, hydroxyl, acetamido or amino, R(4)' denotes hydrogen, R(5) denotes hydrogen or hydroxyl, m denotes 1, 2 or 3, n denotes 0 or 1, p denotes 1, 2, 3 or 4 and R(6) denotes one of the following groups

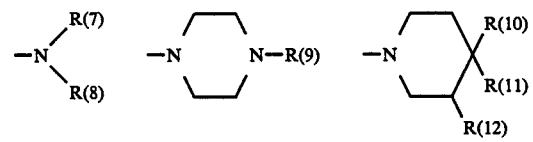

in which

R(7) denotes hydrogen, methyl, ethyl, propyl or isopropyl,

R(8) denotes hydrogen, methyl, ethyl, propyl, isopropyl, cyclopentylethyl, cyclohexylethyl, phenyl-$(C_1-C_4)$-alkyl, the phenyl radical being unsubstituted or substituted by one, two or three radicals from the group consisting of $(C_1-C_4)$-alkyl, $(C_1-C_4)$-alkoxy, $(C_1-C_2)$-alkylenedioxy, F, Cl, $CF_3$ and hydroxyl, or pyridyl-$(C_1-C_4)$-alkyl, R(9) denotes hydrogen, straight-chain or branched $(C_1-C_{10})$-alkyl, phenyl, phenyl-$(C_1-C_4)$-alkyl or di-phenyl-$(C_1-C_5)$-alkyl, phenyl-$(C_1-C_4)$-alkanoyl or benzoyl, the phenyl radical in each case being unsubstituted or substituted by one, two or three radicals from the group consisting of $(C_1-C_4)$-alkyl, $(C_1-C_4)$-alkoxy, $(C_1-C_2)$-alkylenedioxy, F, Cl, $CF_3$ and hydroxyl, or pyridyl, pyrimidinyl or $(C_1-C_5)$-alkanoyl, R(10) denotes phenyl or phenyl-$(C_1-C_4)$-alkyl, the phenyl radical in each case being unsubstituted or substituted by one, two or three radicals from the group consisting of $(C_1-C_4)$-alkyl, $(C_1-C_4)$-alkoxy, $(C1-C2)$alkylenedioxy, F, Cl and hydroxyl, R(11) denotes hydrogen, hydroxyl or methoxy, or together with R(12) denotes a bond, and R(12) denotes hydrogen, or together with R(11) denotes a bond.

3. A compound I as claimed in claim 1, wherein

R(1) denotes hydrogen, methyl, methoxy, fluorine or chlorine,

R(1)' and R(1)'' denote hydrogen,

R(2) denotes hydrogen, methyl or ethyl,

R(3) denotes hydrogen, methyl, ethyl, propyl, isopropyl, butyl, sec.-butyl, isobutyl, allyl, cyclopentyl, cyclohexyl, benzyl or phenethyl, the phenyl ring in each case being unsubstituted or substituted by methyl, methoxy, $CF_3$, fluorine, chlorine, methylenedioxy or nitro, R(4) denotes hydrogen, methyl, methoxy, chlorine, nitro or hydroxyl, R(4)' denotes hydrogen, R(5) denotes hydrogen, hydroxyl or $(C_1-C_3)$-alkyl, m denotes 0 or 1, n denotes 0 or 1, p denotes 1, 2, 3 or 4 and R(6) denotes one of the following groups

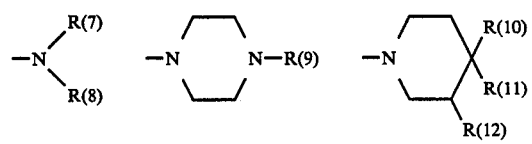

in which

R(7) denotes hydrogen or methyl,

R(8) denotes phenyl-$(C_1-C_4)$-alkyl, the phenyl radical being unsubstituted or substituted by one, two or three radicals from the group consisting of methyl, methoxy, chlorine, methyenedioxy and hydroxyl, R(9) denotes hydrogen, straight-chain or branched $(C_1-C_{10})$-alkyl, phenyl, phenyl-$(C_1-C_4)$-alkyl or di-phenyl-$(C_1-C_5)$-alkyl, phenyl-$(C_1-C_4)$-alkanoyl or benzoyl, the phenyl radical in each case being unsubstituted or substituted by one, two or three radicals from the group consisting of $(C_1-C_4)$-alkyl, $(C_1-C_4)$-alkoxy, $(C_1-C_2)$-alkylenedioxy, F, Cl, $CF_3$ and hydroxyl, or pyridyl, pyrimidinyl or $(C_1-C_5)$-alkanoyl, R(10) denotes phenyl or phenyl-$(C1-C2)$-alkyl, the phenyl radical in each case being unsubstituted or substituted by one, two or three radicals from the group consisting of methyl, methoxy, chlorine, methylenedioxy and hydroxyl, R(11) denotes hydrogen, hydroxyl or methoxy, or together with R(12) denotes a bond, and R(12) denotes hydrogen, or together with R(11) denotes a bond.

4. A compound as claimed in claim 1, wherein

R(1) denotes hydrogen, methyl, methoxy, fluorine or chlorine,

R(1)' and R(1)'' denote hydrogen,

R(2) denotes hydrogen or methyl,

R(3) denotes methyl, ethyl, propyl, isopropyl, butyl, sec.-butyl, isobutyl, cyclopentyl, cyclohexyl or benzyl, unsubstituted or substituted by methoxy, methyl, fluorine, chlorine or nitro, R(4) denotes hydrogen, methoxy, methyl or chlorine, R(5) denotes hydrogen or hydroxyl, m denotes 0 or 1, n denotes 0 or 1, p denotes 1, 2, 3 or 4, R(6) denotes one of the following groups

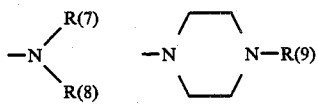

R(7) denotes methyl,

R(8) denotes phenyl-$(C_1-C_4)$-alkyl, the phenyl radical being unsubstituted or substituted by one, two or three radicals from the group consisting of methyl, methoxy, chlorine, methylenedioxy and hydroxyl, R(9) denotes phenyl-$(C_1-C_4)$-alkyl, the phenyl radical being unsubstituted or substituted by one, two or three radicals from the group consisting of $(C_1-C_2)$-alkylenedioxy and hydroxyl, or diphenyl-$(C_1-C_4)$-alkyl, the phenyl radicals being unsubstituted or substituted by chlorine, fluorine or methoxy.

5. an agent for the treatment of disturbances of the calcium balance in the body of a human or warmed-blooded animal, which agent comprises an amount effective for said treatment of at least one compound of formula I as claimed in claim 1 or a salt of said compound with a pharmaceutically acceptable acid together with a pharmaceutically acceptable excipient.

6. A method for the treatment of disturbances of the calcium balance in the body of a human or warm-blooded animal which comprises administering to said human or animal an amount effective for said treatment of at least one compound of formula I as claimed in claim 1 or a salt of said compound with a pharmaceutically acceptable acid together with a pharmaceutically acceptable excipient.

* * * * *